US008709398B2

(12) United States Patent
MacSharry et al.

(10) Patent No.: US 8,709,398 B2
(45) Date of Patent: Apr. 29, 2014

(54) **PROBIOTIC *BIFIDOBACTERIUM* STRAINS**

(75) Inventors: John MacSharry, Cork (IE); Liam O'Mahony, County Cork (IE); David O'Sullivan, County Cork (IE); Barry Kiely, County Cork (IE)

(73) Assignee: Alimentary Health Limited, Cork (IE)

( * ) Notice: Subject to any disclaimer, the term of this patent is extended or adjusted under 35 U.S.C. 154(b) by 952 days.

(21) Appl. No.: 12/450,451

(22) PCT Filed: Mar. 28, 2008

(86) PCT No.: PCT/IE2008/000034
§ 371 (c)(1),
(2), (4) Date: Apr. 26, 2010

(87) PCT Pub. No.: WO2008/117267
PCT Pub. Date: Oct. 2, 2008

(65) Prior Publication Data
US 2011/0020400 A1    Jan. 27, 2011

Related U.S. Application Data

(60) Provisional application No. 60/907,312, filed on Mar. 28, 2007.

(51) Int. Cl.
*A01N 63/00* (2006.01)
*A61K 39/02* (2006.01)
*A61K 39/10* (2006.01)

(52) U.S. Cl.
USPC ...................................... 424/93.4; 424/252.1

(58) Field of Classification Search
None
See application file for complete search history.

(56) References Cited

U.S. PATENT DOCUMENTS

| | | | |
|---|---|---|---|
| 8,034,601 B2* | 10/2011 | Boileau et al. | 435/252.1 |
| 8,137,718 B2* | 3/2012 | Russell et al. | 426/61 |
| 8,557,233 B2* | 10/2013 | MacSharry et al. | 424/93.4 |
| 2005/0074441 A1* | 4/2005 | Collins et al. | 424/93.45 |
| 2005/0175598 A1* | 8/2005 | Boileau et al. | 424/93.45 |
| 2006/0121015 A1* | 6/2006 | Collins et al. | 424/93.45 |
| 2008/0057109 A1* | 3/2008 | Collins et al. | 424/439 |
| 2008/0311080 A1* | 12/2008 | Collins et al. | 424/93.2 |
| 2010/0074871 A1* | 3/2010 | Russell et al. | 424/93.4 |
| 2010/0112003 A1* | 5/2010 | Collins et al. | 424/234.1 |
| 2010/0183559 A1* | 7/2010 | Van Sinderen et al. | 424/93.2 |
| 2011/0020284 A1* | 1/2011 | MacSharry et al. | 424/93.4 |
| 2011/0020400 A1* | 1/2011 | MacSharry et al. | 424/234.1 |
| 2012/0207713 A1* | 8/2012 | MacSharry et al. | 424/93.4 |
| 2012/0276143 A1* | 11/2012 | O'Mahony et al. | 424/234.1 |
| 2013/0004540 A1* | 1/2013 | O'mahony et al. | 424/278.1 |
| 2013/0266539 A1* | 10/2013 | Borody | 424/93.3 |
| 2013/0273015 A1* | 10/2013 | Klassen et al. | 424/93.45 |
| 2013/0280790 A1* | 10/2013 | Vietes Fernandez et al. | 435/252.9 |

FOREIGN PATENT DOCUMENTS

| | | |
|---|---|---|
| EP | 1 481 681 | 12/2004 |
| EP | 1 688 481 | 8/2006 |
| WO | 03/010297 | 2/2003 |
| WO | 2004/076615 | 9/2004 |
| WO | WO 2008/117267 A2 * | 10/2008 |
| WO | WO 2010/055499 A2 * | 5/2010 |
| WO | WO 2011/058535 A1 * | 5/2011 |

OTHER PUBLICATIONS

Imaoka et al, World J. Gastroenterol., Apr. 28, 2008, 14/16:2511-2516.*
Medina et al, British Society for Immunology, Clinical and Experimental Immunology, 2007, 150:531-538.*
Sheil et al, Gastroenterology, Apr. 2007, 132/4, Suppl. 2, p. A209 (abstract only).*
MacSharry et al, Pul. Pharm. And Therap., Aug. 2012, 25/4:325-334.*
Cummings et al, Curr. Issues Intest. Microbiol. (2003) 4: 9-20.*
Fang et al, FEMS Immunology and Medical Microbiology, 2000, 29:47-52.*
Furrie et al, Gut, 2005;54:242-249.*
Macfarlane et al, Current Opinion in Infectious Diseases, 2002, 15:501-506.*
Gibson et al, J. Nutrition, 1995, 125:1401-1412.*
Gionchetti et al, Gastroenterology, 2000;119:305-309.*
International Search Report dated Oct. 7, 2008.
Fang He et al., "Stimulation of the Secretion of Pro-Inflammatory Cytokines by Bifidobacterium Strains," Microbiol. Immunol., 46(11) pp. 781-785 (2002).
Ulf Helwig et al., "Lactobacilli, bifidobacteria and E. coli nissle induce pro-and anti-inflammatory cytokines in peripheral blood mononuclear cells," World Journal of Gastroenterology 12(37), pp. 5978-5986 (Oct. 7, 2006).
Y. Nakamura et al., "Agent for preventing and/or treating allergies, comprises Bifidobacterium, or its processed substance chose from e.g. culture, concentrate and paste of Bifidobacterium, as an active ingredient," 2006(80) XP002478986 (Oct. 12, 2006).
Tadahiko Shiba et al., "The Suppressive Effect of Bifidobacteria on Bacteroides vulgatus, a Putative Pathogenic Microbe in Inflammatory Bowel Disease," Microbiol Immunol. 47(6) pp. 371-378 (2003).
Arai Ki et al., "Cytokines: coordinators of immune and inflammatory responses," Annu. Rev. Biochem., 1990, vol. 59, pp. 783-836.
Crabbe P.A. et al., "The normal microbial flora as a major stimulus for proliferation of plasma cells synthesizing IgA in the gut. The germ free intestinal tract," Intro. Arch. Allergy Appl. Immunol., 1968, vol. 34, pp. 362-375.
de Waal Malefyt et al., "Interleukin 10 (IL-10) and viral IL-10 strongly reduce antigen-specific human T cell proliferation by diminishing the antigen-presenting capacity of monocytes via downregulation of class II major histocompatibility complex expression," J. Exp. Med., Oct. 1, 1991, vol. 174, No. 4, pp. 915924.

(Continued)

*Primary Examiner* — Nita M Minnifield
(74) *Attorney, Agent, or Firm* — Jacobson Holman PLLC

(57) ABSTRACT

Probiotic *Bifidobacterium* strain AH1205 or mutants or variants thereof are immunomodulatory following oral consumption and are useful in the prophylaxis and/or treatment of inflammatory activity such as undesirable gastrointestinal inflammatory activity for example inflammatory bowel disease.

22 Claims, 7 Drawing Sheets

(56) References Cited

OTHER PUBLICATIONS

Henderson B. et al., "Bacteria-Cytokine interactions in health and disease," Portland Press, 1998, pp. 79-130.

Kagnoff M.F. et al., "Immunology of the intestinal tract," Gastroenterol., 1993, vol. 105, No. 5, pp. 1275-1280.

Lamm M.E., "Interaction of antigens and antibodies at mucosal surfaces," Ann. Rev. Micobiol., 1997, vol. 51, pp. 311-340.

Marson A. et al., "Foxp3 occupancy and regulation of key target genes during T-cell stimulation," Letters to Nature, Feb. 22, 2007, vol. 445, No. 7130, pp. 931-935.

Masco L. et al., "Identification of *Bifidobacterium* species using rep-PCR fingerprinting," Syst. Appl. Micobiol., Nov. 2003, vol. 26, No. 4, pp. 557-563.

McCracken V.J. et al., "Probiotics a critical review," Tannock, GW (ed), Horizon Scientific Press, UK, 1999, pp. 85-113.

McGee DW et al., "A synergistic relationship between TNF-alpha, IL-1 beta, and TGF-beta 1 on IL-6 secretion by the IEC-6 intestinal epithelial cell line," Immunology, Sep. 1995, vol. 86, No. 1, pp. 6-11.

Medaglini D. et al., "Mucosal and systemic immune responses to a recombinant protein expressed on the surface of the oral commensal bacterium *Streptococcus gordonii* after oral colonization," Proc. Natl. Acad. Sci USA, 1995, vol. 92, pp. 6868-6872.

Raychaudhuri S. et al., "Fully mobilizing host defense: building better vaccines," Nat biotechnol., 1998, vol. 16, pp. 1025-1031.

Rowland I.R., "Human colonic bacteria: role in nutrition, physiology and pathology," Gibson G.R. (ed), Boca Raton CRC Press, 1995, pp. 155-174.

Savage D.C., "Microbial Ecology of the Gut," Clark and Bauchop (eds), Academic Press, 1977, London, pp. 277-310.

Stallmach A. et al., "Induction and modulation of gastrointestinal inflammation," Immunol. Today, 1998, vol. 19, No. 10, pp. 438-441.

Steidler L. et al., "Mucosal delivery of murine interleukin-2 (IL-2) and IL-6 by recombinant strains of *Lactococcus lactis* coexpressing antigen and cytokine," Infect. Immun., 1998, vol. 66 pp. 3183-3189.

Tagg Jr et al., "Bacteriocins of Gram positive bacteria," Bacteriol. Rev., 1976, vol. 40, pp. 722-756.

Walker R.I., "New strategies for using mucosal vaccination to achieve more effective immunization," Vaccine, 1994, vol. 12, pp. 387-400.

Wu S. et al., "Transfection of ovarian cancer cells with tumour necrosis factor alpha (TNF-alpha) antisense mRNA abolishes the proliferative response to interleukin-1 (IL-1) but not TNF-alpha," Gynecol. Oncol., Apr. 1994, vol. 53, No. 1, pp. 59-63.

\* cited by examiner

SEQUENCE LISTING

```
<160> NUMBER OF SEQ ID NOS: 5

<210> SEQ ID NO 1
<211> LENGTH: 494
<212> TYPE: DNA
<213> ORGANISM: Bifidobacterium longum
<220> FEATURE:
<221> NAME/KEY: misc_feature
<222> LOCATION:
<223> OTHER INFORMATION: n can be any of a,c,g or t

<400> SEQUENCE: 1
gcctagnctt ncngncacac gtcaccacac ggtgtcgcat ggccccgntn ggcatccttc      60
ctagcaaatt cccaggacga caaatcatca cactaaaatg atcacaaaac gatcgaaaca    120
aacactaaaa atagagttng attngaaatt aacagcaaga acgaggaatn aaaggnaacc    180
ccgtnttgnt tgngtccact atncagtttt naagccacca cgcaccacca cgccgtncgg    240
acgggaccag cccgccatna ggnacgatgg gcatngaatc gcgccaggnc aaancctggg    300
gtggcgatnc gggagcccaa aagcgcatnc acaccactnc cgcggaacat nccacgacgg    360
acgcaccgna agnccatgat tttttncaca ccancagccc caagncgccg cgactgncgc    420
gacgccnggg ctcgcaccgc cngacgaaca tncggncgtn ttntncgtan aaaggaggtt    480
cccancnann ncng                                                      494

<210> SEQ ID NO 2
<211> LENGTH: 479
<212> TYPE: DNA
<213> ORGANISM: Bifidobacterium longum
<220> FEATURE:
<221> NAME/KEY: misc_feature
<222> LOCATION:
<223> OTHER INFORMATION: n can be any of a,c,g or t

<400> SEQUENCE: 2
aananaaacg ccgcngttct ccgcggtgcg tgccccgtcg tcncggcagt cgcggcggcc      60
tggggctgct ggtgtggaag agatcatggg ctttcggtgc gtccgtcntg ggatgttccg    120
cgggagtggt gtgnatgcgc ttttggnctc ccggatcgcc accncaggct ttggcctggc    180
gcgattcgat gcccatcgtg cctgatggcg ggctggtccc gtccggacgg cntggtggtg    240
cgtggtggct tgagaactgg atagtggacg cgagcaagac ngggtttcct ttgattcctc    300
ttcttgctgt tgatttcgaa tcgaactcta tttttantgt ttgnttccat cgttttgtga    360
ncattttaat gtganganntt gtcctctggg aatttgctan gaanganccct tgnngccang  420 cncaccntgn ngnncctgtt gcctgcaang gcgnanggng gaagcccttg canccagaa    479

<210> SEQ ID NO 3
<211> LENGTH: 18
<212> TYPE: DNA
<213> ORGANISM: Artificial Sequence
<220> FEATURE:
<223> OTHER INFORMATION: Primer
```

```
<400> SEQUENCE: 3
gctggatcac ctcctttc                                                    18

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
ctggtgccaa ggcatcca                                                    18

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ctacggcaag gcgacgctga cg                                               22
```

PROBIOTIC *BIFIDOBACTERIUM* STRAINS

This is a national stage of PCT/IE08/000,034 filed Mar. 28, 2008 and published in English, claiming benefit of U.S. provisional application No. 60/907,312, filed Mar. 28, 2007, hereby incorporated by reference.

The invention relates to a *Bifidobacterium* strain and its use as a probiotic bacteria in particular as an immunomodulatory biotherapeutic agent.

The defense mechanisms to protect the human gastrointestinal tract from colonization by intestinal bacteria are highly complex and involve both immunological and non-immunological aspects (1). Innate defense mechanisms include the low pH of the stomach, bile salts, peristalsis, mucin layers and anti-microbial compounds such as lysozyme (2). Immunological mechanisms include specialized lymphoid aggregates, underlying M cells, called peyers patches which are distributed throughout the small intestine and colon (3). Luminal antigens presented at these sites result in stimulation of appropriate T and B cell subsets with establishment of cytokine networks and secretion of antibodies into the gastrointestinal tract (4). In addition, antigen presentation may occur via epithelial cells to intraepithelial lymphocytes and to the underlying lamina propria immune cells (5). Therefore, the host invests substantially in immunological defense of the gastrointestinal tract. However, as the gastrointestinal mucosa is the largest surface at which the host interacts with the external environment, specific control mechanisms must be in place to regulate immune responsiveness to the 100 tons of food which is handled by the gastrointestinal tract over an average lifetime. Furthermore, the gut is colonized by over 500 species of bacteria numbering $10^{11}$-$10^{12}$/g in the colon. Thus, these control mechanisms must be capable of distinguishing non-pathogenic adherent bacteria from invasive pathogens, which would cause significant damage to the host. In fact, the intestinal flora contributes to defense of the host by competing with newly ingested potentially pathogenic micro-organisms.

Bacteria present in the human gastrointestinal tract can promote inflammation. Aberrant immune responses to the indigenous microflora have been implicated in certain disease states, such as inflammatory bowel disease. Antigens associated with the normal flora usually lead to immunological tolerance and failure to achieve this tolerance is a major mechanism of mucosal inflammation (6). Evidence for this breakdown in tolerance includes an increase in antibody levels directed against the gut flora in patients with inflammatory bowel disease (IBD).

The present invention is directed towards a *Bifidobacterium* strain which has been shown to have immunomodulatory effects, by modulating cytokine levels or by antagonizing and excluding pro-inflammatory micro-organisms from the gastrointestinal tract.

STATEMENTS OF INVENTION

According to the invention there is provided *Bifidobacterium* strain AH1205 (NCIMB41387) or mutants or variants thereof.

The mutant may be a genetically modified mutant. The variant may be a naturally occurring variant of *Bifidobacterium*.

The strain may be a probiotic. It may be in the form of a biologically pure culture.

The invention also provides an isolated strain of *Bifidobacterium* NCIMB 41387

In one embodiment of the invention *Bifidobacterium* strains are in the form of viable cells. Alternatively *Bifidobacterium* strains are in the form of non-viable cells.

In one embodiment of the invention the *Bifidobacterium* strains are isolated from infant faeces, the *Bifidobacterium* strains being significantly immunomodulatory following oral consumption in humans.

The invention also provides a formulation which comprises the *Bifidobacterium* strain of the invention.

In one embodiment of the invention the formulation includes another probiotic material.

In one embodiment of the invention the formulation includes a prebiotic material.

Preferably the formulation includes an ingestable carrier. The ingestable carrier may be a pharmaceutically acceptable carrier such as a capsule, tablet or powder. Preferably the ingestable carrier is a food product such as acidified milk, yoghurt, frozen yoghurt, milk powder, milk concentrate, cheese spreads, dressings or beverages.

In one embodiment of the invention the formulation of the invention further comprises a protein and/or peptide, in particular proteins and/or peptides that are rich in glutamine/glutamate, a lipid, a carbohydrate, a vitamin, mineral and/or trace element.

In one embodiment of the invention the *Bifidobacterium* strain is present in the formulation at more than $10^6$ cfu per gram of delivery system. Preferably the formulation includes any one or more of an adjuvant, a bacterial component, a drug entity or a biological compound.

In one embodiment of the invention the formulation is for immunisation and vaccination protocols.

The invention further provides a *Bifidobacterium* strain or a formulation of the invention for use as foodstuffs, as a medicament, for use in the prophylaxis and/or treatment of undesirable inflammatory activity, for use in the prophylaxis and/or treatment of undesirable respiratory inflammatory activity such as asthma, for use in the prophylaxis and/or treatment of undesirable gastrointestinal inflammatory activity such as inflammatory bowel disease eg. Crohns disease or ulcerative colitis, irritable bowel syndrome, pouchitis, or post infection colitis, for use in the prophylaxis and/or treatment of gastrointestinal cancer(s), for use in the prophylaxis and/or treatment of systemic disease such as rheumatoid arthritis, for use in the prophylaxis and/or treatment of autoimmune disorders due to undesirable inflammatory activity, for use in the prophylaxis and/or treatment of cancer due to undesirable inflammatory activity, for use in the prophylaxis of cancer, for use in the prophylaxis and/or treatment of diarrhoeal disease due to undesirable inflammatory activity, such as *Clostridium difficile* associated diarrhoea, Rotavirus associated diarrhoea or post infective diarrhoea, for use in the prophylaxis and/or treatment of diarrhoeal disease due to an infectious agent, such as *E. coli*.

The invention also provides a *Bifidobacterium* strain or a formulation of the invention for use in the preparation of an anti-inflammatory biotherapeutic agent for the prophylaxis and/or treatment of undesirable inflammatory activity or for use in the preparation of anti-inflammatory biotherapeutic agents for the prophylaxis and/or treatment of undesirable inflammatory activity.

In one embodiment of the invention the strain of the invention act by antagonising and excluding proinflammatory micro-organisms from the gastrointestinal tract.

The invention also provides a *Bifidobacterium* strain or a formulation of the invention for use in the preparation of anti-inflammatory biotherapeutic agents for reducing the levels of pro-inflammatory cytokines.

The invention further provides a *Bifidobacterium* strain for use in the preparation of anti-inflammatory biotherapeutic agents for modifying the levels of IL-10.

The invention also provides for the use of a *Bifidobacterium* strain as a anti-infective probiotic due to their ability to antagonise the growth of pathogenic species.

We have found that particular strains of *Bifidobacterium* elicit immunomodulatory effects in vitro.

The invention is therefore of major potential therapeutic value in the prophylaxis or treatment of dysregulated immune responses, such as undesirable inflammatory reactions for example asthma.

*Bifidobacterium* are commensal microorganisms. They have been isolated from the microbial flora within the human gastrointestinal tract. The immune system within the gastrointestinal tract cannot have a pronounced reaction to members of this flora, as the resulting inflammatory activity would also destroy host cells and tissue function. Therefore, some mechanism(s) exist whereby the immune system can recognize commensal non-pathogenic members of the gastrointestinal flora as being different to pathogenic organisms. This ensures that damage to host tissues is restricted and a defensive barrier is still maintained.

A deposit of *Bifidobacterium longum* strain AH1205 was made at the NCIMB on May 11, 2006 and accorded the accession number NCIMB 41387.

The *Bifidobacterium longum* may be a genetically modified mutant or it may be a naturally occurring variant thereof.

Preferably the *Bifidobacterium longum* is in the form of viable cells.

Alternatively the *Bifidobacterium longum* may be in the form of non-viable cells.

It will be appreciated that the specific *Bifidobacterium* strain of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound.

In addition a vaccine comprising the strains of the invention may be prepared using any suitable known method and may include a pharmaceutically acceptable carrier or adjuvant.

Throughout the specification the terms mutant, variant and genetically modified mutant include a strain of Bifidobacteria whose genetic and/or phenotypic properties are altered compared to the parent strain. Naturally occurring variant of *Bifidobacterium longum* includes the spontaneous alterations of targeted properties selectively isolated. Deliberate alteration of parent strain properties is accomplished by conventional (in vitro) genetic manipulation technologies, such as gene disruption, conjugative transfer, etc. Genetic modification includes introduction of exogenous and/or endogenous DNA sequences into the genome of a Bifidobacteria strain, for example by insertion into the genome of the bacterial strain by vectors, including plasmid DNA, or bacteriophages.

Natural or induced mutations include at least single base alterations such as deletion, insertion, transversion or other DNA modifications which may result in alteration of the amino acid sequence encoded by the DNA sequence.

The terms mutant, variant and genetically modified mutant also include a strain of Bifidobacteria that has undergone genetic alterations that accumulate in a genome at a rate which is consistent in nature for all micro-organisms and/or genetic alterations which occur through spontaneous mutation and/or acquisition of genes and/or loss of genes which is not achieved by deliberate (in vitro) manipulation of the genome but is achieved through the natural selection of variants and/or mutants that provide a selective advantage to support the survival of the bacterium when exposed to environmental pressures such as antibiotics. A mutant can be created by the deliberate (in vitro) insertion of specific genes into the genome which do not fundamentally alter the biochemical functionality of the organism but whose products can be used for identification or selection of the bacterium, for example antibiotic resistance.

A person skilled in the art would appreciate that mutant or variant strains of Bifidobacteria can be identified by DNA sequence homology analysis with the parent strain. Strains of Bifidobacteria having a close sequence identity with the parent strain are considered to be mutant or variant strains. A Bifidobacteria strain with a sequence identity (homology) of 96% or more, such as 97% or more, or 98% or more, or 99% or more with the parent DNA sequence may be considered to be a mutant or variant. Sequence homology may be determined using on-line homology algorithm "BLAST" program, publicly available at http://www.ncbi.nlm.nih.gov/BLAST/.

Mutants of the parent strain also include derived Bifidobacteria strains having at least 85% sequence homology, such as at least 90% sequence homology, or at least 95% sequence homology to the 16s-23s intergenic spacer polynucleotide sequence of the parent strain. These mutants may further comprise DNA mutations in other DNA sequences in the bacterial genome.

DETAILED DESCRIPTION

Figure 1:
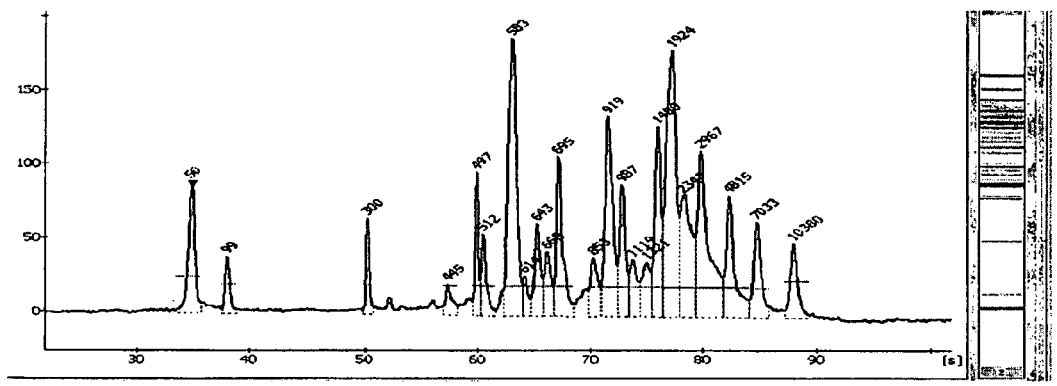
FIG. 1 is a BOX PCR (BIOANALYZER) barcode profile for *B. longum* AH1205. Base pair sizes were determined using the AGILENT 2100 software.

We have found that *Bifidobacterium longum* strain AH1205 is not only acid and bile tolerant and transits the gastrointestinal tracts but also, surprisingly has immunomodulatory effects, by modulating cytokine levels or by antagonising and excluding pro-inflammatory or immunomodulatory micro-organisms from the gastrointestinal tract.

The general use of probiotic bacteria is in the form of viable cells. However, it can also be extended to non-viable cells such as killed cultures or compositions containing beneficial factors expressed by the probiotic bacteria. This could include thermally killed micro-organisms or micro-organisms killed by exposure to altered pH or subjection to pressure. With non-viable cells product preparation is simpler, cells may be incorporated easily into pharmaceuticals and storage requirements are much less limited than viable cells. *Lactobacillus casei* YIT 9018 offers an example of the effective use of heat killed cells as a method for the treatment and/or prevention of tumour growth as described in U.S. Pat. No. 4,347,240.

It is unknown whether intact bacteria are required to exert an immunomodulatory effect or if individual active components of the invention can be utilized alone. Proinflammatory components of certain bacterial strains have been identified. The proinflammatory effects of gram-negative bacteria are mediated by lipopolysaccharide (LPS). LPS alone induces a proinflammatory network, partially due to LPS binding to the CD14 receptor on monocytes. It is assumed that components of probiotic bacteria possess immunomodulatory activity, due to the effects of the whole cell. Upon isolation of these components, pharmaceutical grade manipulation is anticipated.

IL-10 is produced by T cells, B cells, monocytes and macrophages. This cytokine augments the proliferation and differentiation of B cells into antibody secreting cells. IL-10 exhibits mostly anti-inflammatory activities. It up-regulates IL-1RA expression by monocytes and suppresses the majority of monocyte inflammatory activities. IL-10 inhibits monocyte production of cytokines, reactive oxygen and nitrogen intermediates, MHC class II expression, parasite killing and IL-10 production via a feed back mechanism (7). This cytokine has also been shown to block monocyte production of intestinal collagenase and type IV collagenase by interfering with a $PGE_2$-cAMP dependant pathway and therefore may be an important regulator of the connective tissue destruction seen in chronic inflammatory diseases.

The host response to infection is characterised by innate and acquired cellular and humoral immune reactions, designed to limit spread of the offending organism and to restore organ homeostasis. However, to limit the aggressiveness of collateral damage to host tissues, a range of regulatory constraints may be activated. Regulatory T cells (Tregs) serve one such mechanism. These are derived from the thymus but may also be induced in peripheral organs, including the gut mucosa. Deliberate administration of Treg cells suppresses inflammatory disease in a wide range of murine models including experimental autoimmune encephalomyelitis, inflammatory bowel disease, bacterial-induced colitis, collagen-induced arthritis, type I diabetes, airway osinophilic inflammation, graft-vs-host disease and organ transplantation. The forkhead transcription factor Foxp3 (forkhead box P3) is selectively expressed in Treg cells, is required for Treg development and function, and is sufficient to induce a Treg phenotype in conventional CD4 cells (19). Mutations in Foxp3 cause severe, multi-organ autoimmunity in both human and mouse. We have described a *Bifidobacterium* strain that generates CD25 positive/Foxp3 positive T regulatory cells in vivo.

The invention will be more clearly understood from the following examples.

EXAMPLE 1

Characterisation of Bacteria Isolated from Infant Faeces

Demonstration of Probiotic Traits

Isolation of Probiotic Bacteria

Fresh faeces was obtained from a 3 day old male breast fed infant and serially dilutions were plated on TPY (trypticase, peptone and yeast extract) and MRS (deMann, Rogosa and Sharpe) media supplemented with 0.05% cysteine and mupirocin. Plates were incubated in anaerobic jars (BBL, Oxoid) using $CO_2$ generating kits (Anaerocult A, Merck) for 2-5 days at 37° C. Gram positive, catalase negative rod-shaped or bifurcated/pleomorphic bacteria isolates were streaked for purity on to complex non-selective media (MRS and TPY). Isolates were routinely cultivated in MRS or TPY medium unless otherwise stated at 37° C. under anaerobic conditions. Presumptive *Bifidobacterium* were stocked in 40% glycerol and stored at –20° C. and –80° C.

Following isolation of a pure bifidobacteria strain, assigned the designation AH1205, microbiological characteristics were assessed and are summarized in Table 1 below. AH1205 is a gram positive, catalase negative pleomorphic shaped bacterium which is Fructose-6-Phoshate Phosphoketolase positive confirming its identity as a *bifidobacterium*. Using minimal media in which a single carbon source was inserted, AH1205 was able to grow on all carbon sources tested (Glucose, Lactose, Ribose, Arabinose, Galactose, Raffinose, Fructose, Malt Extract, Mannose, Maltose, Sucrose).

TABLE 1

Physiochemical characteristics of *B. longum* AH1205

| | *B. longum* AH1205 |
|---|---|
| Strain Characteristics | |
| Gram Stain | + |
| Catalase | − |
| Motility | − |
| F6PPK* | + |
| Milk coagulation | + |
| 45° C. anaerobic culture | − |
| 45° C. aerobic culture | − |
| CHO Fermentation: | |
| Glucose | + |
| Lactose | + |
| Ribose | + |
| Arabinose | + |
| Galactose | + |
| Raffinose | + |
| Fructose | + |
| Malt Extract | + |
| Mannose | + |
| Maltose | + |
| Sucrose | + |

*signifies Fructose-6-Phoshate Phosphoketolase Assay

Species Identification 16s intergenic spacer (IGS) sequencing was performed to identify the species of bifidobacteria isolated. Briefly, DNA was isolated from AH1205 using 100 µl of Extraction Solution and 25 µl of Tissue Preparation solution (Sigma, XNAT2 Kit). The samples were incubated for 5 minutes at 95° C. and then 100 µl of Neutralization Solution (XNAT2 kit) was added. Genomic DNA solution was quantified using a NANODROP spectrophotometer and stored at 4° C. PCR was performed using the IGS primers, IGS L: 5'-GCTGGAT-CACCTCCTTTC-3' (SEQ ID NO. 3) which is based on SEQ ID NO. 1 and IGS R: 5'-CTGGTGCCAAGGCATCCA-3' (SEQ ID NO. 4) which is based on SEQ ID NO. 2. The cycling conditions were 94° C. for 3 min (1 cycle), 94° C. for 30 sec, 53° C. for 30 sec, 72° C. for 30 sec (28 cycles). The PCR reaction contained 4 µl (50 ng) of DNA, PCR mix (XNAT2 kit), 0.4 µM IGS L and R primer (MWG Biotech, Germany). The PCR reactions were performed on an EPPENDORF THERMOCYCLER. The PCR products (10 µl) were ran alongside a molecular weight marker (100 bp Ladder, Roche) on a 2% agarose EtBr stained gel in TAE, to determine the IGS profile. PCR products of *Bifidobacterium* (single band) were purified using the PROMEGA WIZARD PCR purification kit. The purified PCR products were sequenced using the primer sequences (above) for the intergenic spacer region. Sequence data was then searched against the NCBI nucleotide database to determine the identity of the strain by nucleotide homology. The resultant DNA sequence data was subjected to the NCBI standard nucleotide-to-nucleotide homology BLAST search engine (http://www.ncbi.nlm.nih.gov/BLAST/). The nearest match to the sequence was identified and then the sequences were aligned for comparison using DNASTAR MegAlign software. The sequences (SEQ ID NO. 1 [IGS forward sequence] and SEQ ID NO. 2 [IGS reverse sequence]) obtained can be viewed in the sequence listing. Searching the NCIMB database revealed that AH1205 has a unique IGS (SEQ ID NO. 1 [forward sequence] and SEQ ID NO. 2 [reverse sequence]) sequence with its closest sequence homology to a *Bifidobacterium longum*.

In order to develop a barcode PCR profile for AH1205, PCR was performed using BOX primers (8). The cycling conditions were 94° C. for 7 min (1 cycle); 94° C. for 1 minute, 65° C. for 8 minutes, (30 cycles) and 65° C. for 16 minutes. The PCR reaction contained 50 ng of DNA, PCR mix (XNAT2 kit) and 0.3 µM BOXA1R primer (5'-CTACG-GCAAGGCGACGCTGACG-3') (SEQ ID NO. 5) (MWG Biotech, Germany). The PCR reactions were performed on an EPPENDORF THERMOCYCLER. The PCR products (1 µl) were ran alongside a molecular weight marker (DNA 7500 ladder, Agilent, Germany) using the DNA 7500 LABCHIP on the AGILENT 2100 BIOANALYZER (Agilent, Germany). The barcode (PCR product profile) was determined using the AGILENT BIOANALYZER software where peak number (PCR products) and size were identified (FIG. 1).

Antibiotic Sensitivity Profiles

Antibiotic sensitivity profiles of the *B. longum* strain was determined using the 'disc susceptibility' assay. Cultures were grown up in the appropriate broth medium for 24-48 h spread-plated (100 µl) onto agar media and discs containing known concentrations of the antibiotics were placed onto the agar. Strains were examined for antibiotic sensitivity after 1-2 days incubation at 37° C. under anaerobic conditions. Strains were considered sensitive if zones of inhibition of 1 mm or greater were seen. The minimum inhibitory concentration (MIC) for each antibiotic was independently assessed. The MIC for clindamycin, vancomycin and metronidazole were 0.032, 0.75 and >256 respectively.

Intestinal Transit

To determine whether *Bifidobacterium longum* could survive at low pH values equivalent to those found in the stomach, bacterial cells were harvested from fresh overnight cultures, washed twice in phosphate buffer (pH 6.5) and resuspended in TPY broth adjusted to pH 2.5 (with 1M HCl). Cells were incubated at 37° C. and survival measured at intervals of 5, 30, 60 and 120 minutes using the plate count method. AH1205 survived well for 5 minutes at pH 2.5 while no viable cells were recovered after 30 minutes.

Upon exiting the stomach, putative probiotics are exposed to bile salts in the small intestine. In order to determine the ability of *B. longum* to survive exposure to bile, cultures were streaked on TPY agar plates supplemented with 0.3% (w/v), 0.5%, 1%, 2%, 5%, 7.5% or 10% porcine bile. *B. longum* AH1205 growth was observed on plates containing up to 0.5% bile.

Figure 2:
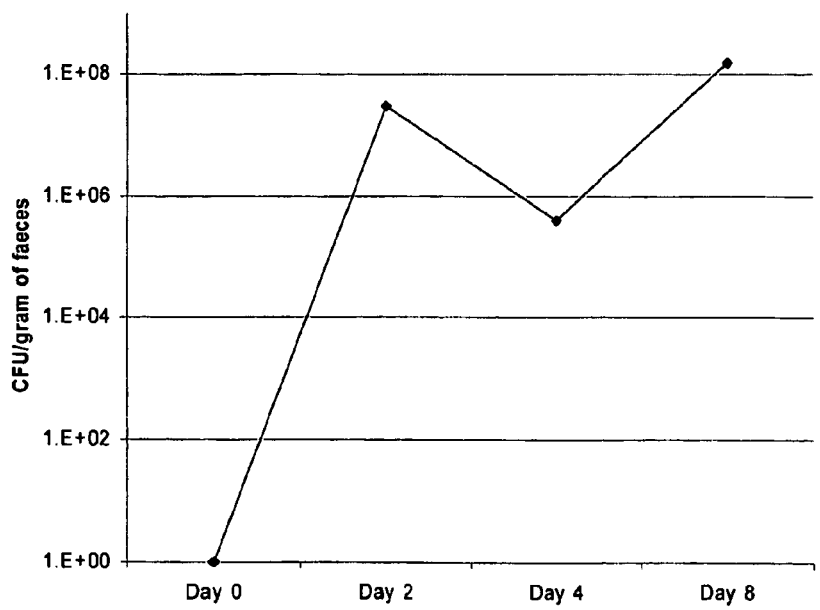
FIG. 2 is a graph illustrating the faecal recovery of *B. longum* AH1205 over an 8 day feeding period which demonstrates the ability of AH1205 to transit the murine gastrointestinal tract.

In a murine model, the ability of *B. longum* AH1205 to transit the gastrointestinal tract was assessed. Mice consumed $1 \times 10^9$ AH1205 daily and faecal pellets were examined for the presence of the fed micro-organism. Detection of AH1205 was facilitated by isolating a spontaneous rifampicin resistant variant of the bifidobacteria—incorporation of rifampicin in the TPY plates used to assess transit ensured that only the fed rifampicin resistant bifiobacteria was cultured. Faecal samples were collected daily and *B. longum* transit through the gastrointestinal tract was confirmed (FIG. 2).

Anti-Microbial Activity

The indicator pathogenic micro-organisms used in this study were propagated in the following medium under the following growth conditions: *Salmonella typhimurium* (37° C., aerobic) in Tryptone Soya broth/agar supplemented with 0.6% yeast extract (TSAYE, Oxoid), *Campylobacter jejuni* (37° C., anaerobic) and *E. coli* O157:H7 (37° C., anaerobic) on Blood agar medium, *Clostridium difficile* (37° C., anaerobic) in reinforced Clostridial medium (RCM, Oxoid). All strains were inoculated into fresh growth medium and grown overnight before being used in experiments.

Antimicrobial activity was detected using the deferred method (9). Briefly, *B. longum* AH1205 was incubated for 36-48 h. Ten-fold serial dilutions were spread-plated (100 µl) onto TPY agar medium. After overnight incubation, plates with distinct colonies were overlayed with the indicator bacterium. The indicator lawn was prepared by inoculating a molten overlay with 2% (v/v) of an overnight indicator culture which was poured over the surface of the inoculated TPY plates. The plates were re-incubated overnight under conditions suitable for growth of the indicator bacterium. Indicator cultures with inhibition zones greater than 1 mm in radius were considered sensitive to the test bacterium. *B. longum* AH1205 inhibited the growth of all pathogenic organisms tested, with zones of clearing measuring 8.67, >80, 4.33 and 11.67 mm for *Salmonella typhimurium, Campylobacter jejuni, E. coli* O157:H7 and *Clostridium difficile* respectively.

EXAMPLE 2

Cytokine Production by PBMCs in Response to *B. Longum*

Figure 3:
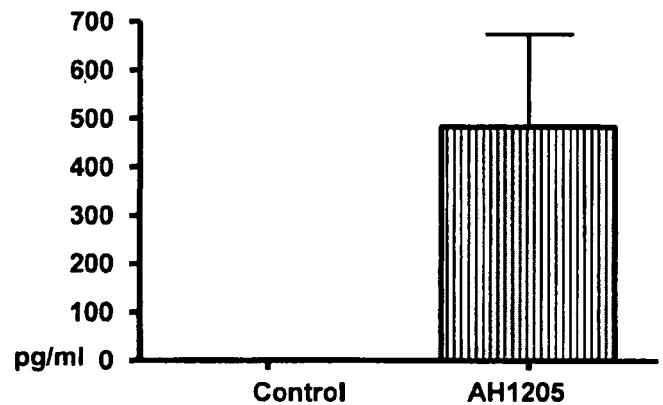
FIG. 3 is a bar graph showing the effect of *B. longum* AH1205 on IL-10 cytokine production by human PBMCs. Results are expressed as mean+/−SE (n=6).

Peripheral blood mononuclear cells (PBMCs) were isolated from healthy donors by density gradient centrifugation. PBMCs were stimulated with the probiotic bacterial strain for a 72 hour period at 37° C. At this time culture supernatants were collected, centrifuged, aliquoted and stored at −70° C. until being assessed for IL-10 levels using cytometric bead arrays (BD BioSciences). AH1205 induced significant secretion of IL-10 by human PBMCs suggesting this probiotic strain would induce a anti-inflammatory response in vivo (FIG. 3).

EXAMPLE 3

*B. Longum* AH1205 Attenuates Respiratory Disease in a Murine Model of Asthma

This study investigated whether the probiotic bacteria *Bifidobacterium longum* AH1205, suppress allergic responses in an ovalbumin (OVA) sensitized mouse model of allergic airway inflammation. Briefly, adult male BALB/c mice were sensitized by i.p. injection of OVA day 0 and day 6. On days 12 and 14, mice were challenged intranasally with OVA. Twenty-four hours after the last challenge (day 15), mice were subjected to measurements of airway responsiveness followed by BAL procedure. OVA/alum-sensitized, saline-challenged mice served as controls. Animals received probiotic or placebo throughout the trial. Airway inflammation (cytokine and cell counts) was assessed by inflammatory cell counts in bronchoalveolar lavage (BAL) fluid. Airway responsiveness was also measured using the Buxco whole-body plethysmograph. Splenocytes were also isolated from OVA sensitized mice and were incubated in the presence of anti-CD3 and anti-CD28 antibodies after which cytokine levels were measured in the supernatants by flow cytometry.

Figure 4:
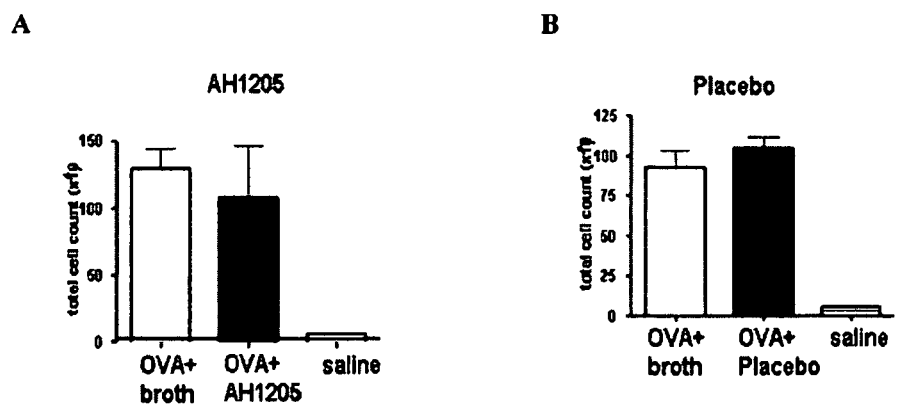
FIGS. 4 A and B are graphs showing the effect of probiotic bacterial strain AH1205 (A) and placebo (B) on total cell numbers in bronchoalveolar lavage fluid following ovalbumin (OVA) challenge in sensitised animals (n=10/group, *=p<0.05 compared to OVA challenge alone).
Figure 5:
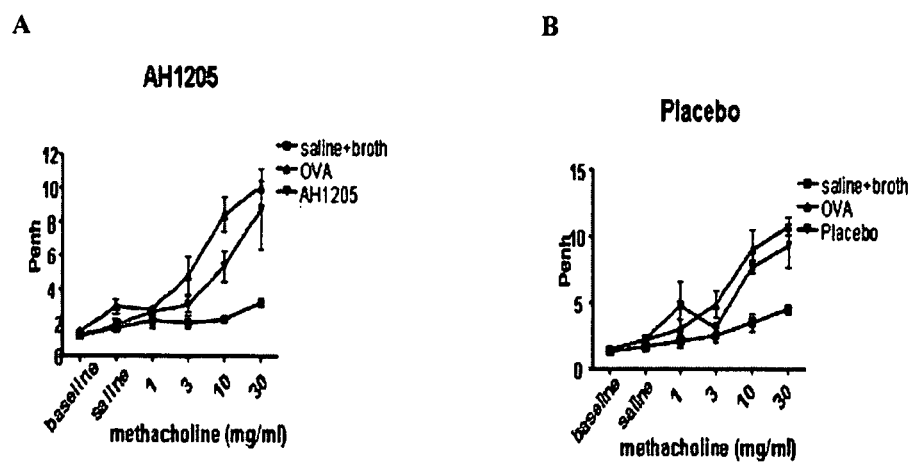
FIGS. 5 A and B are graphs showing the effect of probiotic strain AH1205 treatment (A) and placebo (B) on airway responsiveness to methacholine, as assessed by changes in enhanced pause (Penh) in ovalbumin (OVA)—sensitised mice 24 hours after intranaval challenge with OVA or saline. Each data paint represents the mean±SEM (n=10/groups * p=<0.05 compared to OVA alone).

*B. longum* AH1205 caused no significant reduction in cells recovered from BAL fluid following OVA challenge, when compared to broth fed animals (FIG. 4). Airway responsiveness was measured and challenge of sensitized mice with OVA resulted in an enhancement of AHR to methacholine when compared with saline-challenged mice. AH1205 did not modulate this enhanced airway responsiveness to methacholine, as assessed by changes in enhanced pause (FIG. 5).

Figure 6:
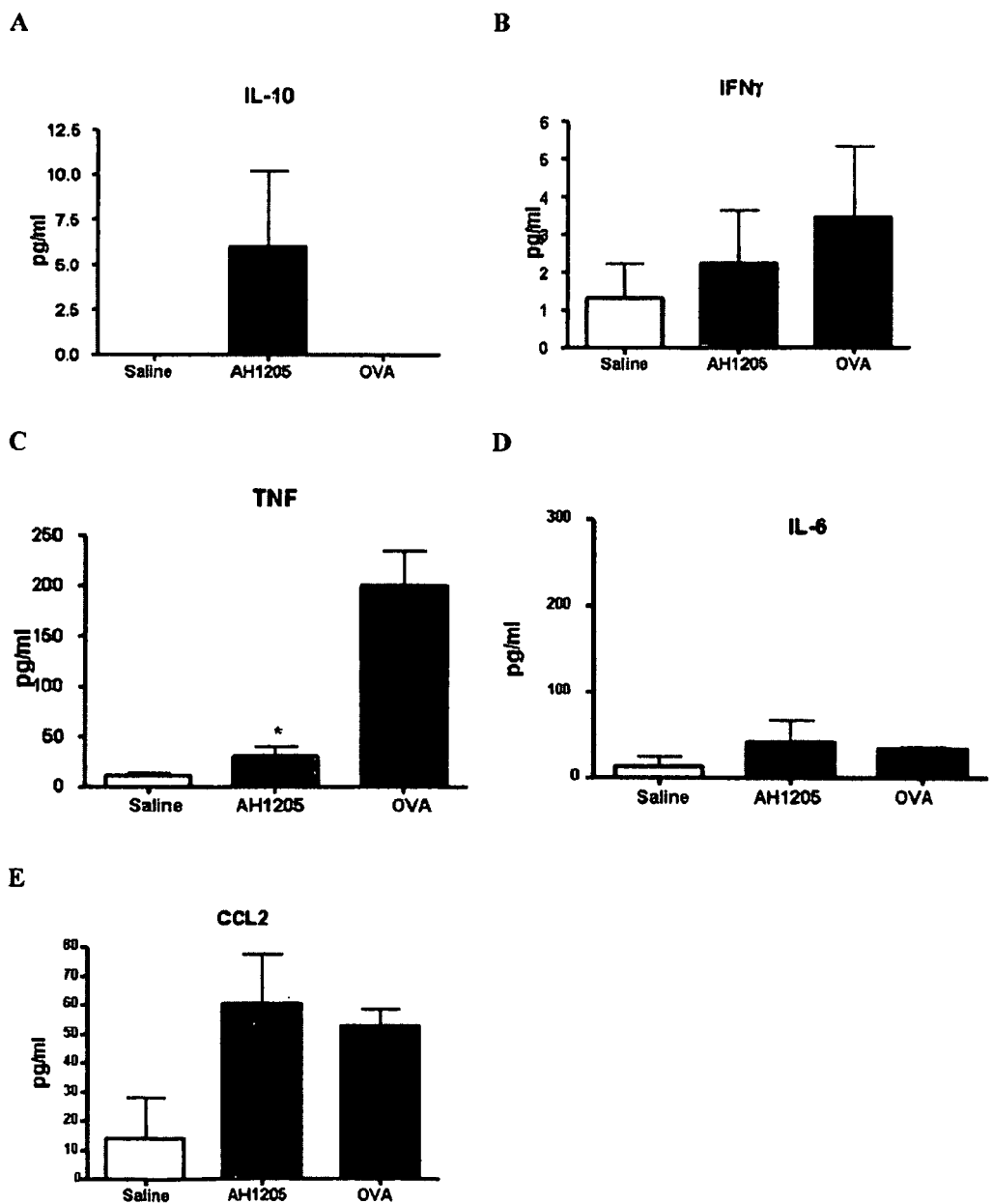
FIG. 6 A to E are graphs showing IL-10(A), IFNγ(B), TNF(C), IL-6(D) and CCL2(E) cytokine levels in bronchoalveolar lavage (BAL) fluid from ovalbumin (OVA)—sensitised mice. Each column represents the mean±SEM (n=10, * p<0.05 compared to OVA challenged, saline treated control).

BAL cytokine levels were measured by cytometric bead array and demonstrated that animals fed AH1205 had significantly reduced TNF-α levels compared to OVA control (FIG. 6C). No significant differences were noted for IL-10, IFN-γ, IL-6 and CCL2 levels. (FIG. 6)

EXAMPLE 4

Treg Effector Model

This study investigated the effect of probiotic consumption on regulatory T cell number and activity in healthy mice. BALB/c mice (10/group) were fed *Bifidobacterium longum* AH1205 or placebo for three weeks. Following probiotic/placebo consumption, CD4+CD25+ T-regulatory cells were isolated and their in vitro suppressive activity was determined by measuring proliferation of anti-CD3/CD28 stimulated CFSE-labelled CD4+ responder T cells using flow cytometry. CD4+ responder T cells were co-incubated with CD4+CD25− T cells as a control. The percentage of CD4+CD25+ cells (Regulatory T cells) in murine splenocytes that are also FoxP3 positive was determined in the spleens of probiotic or placebo-fed mice.

Figure 7:
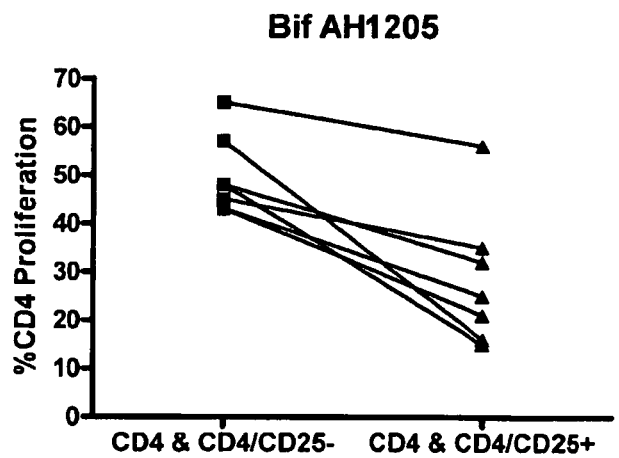
FIG. 7 is a graph illustrating that $CD4^+$ $CD25^+$ Cells from AH1205 fed mice significantly reduced responder CD4 T cell proliferation (n=7).

The % of CD4+ cells that proliferated when co-incubated with CD4+CD25+ cells from the probiotic/placebo fed mice was compared to the % of CD4+ cells that proliferated when co-incubated with CD4+CD25− cells from the same trial mouse. In each case, T cell proliferation was less in cultures containing CD4+CD25+ cells compared in cultures containing CD4 cells alone and depleted of the CD25+ cells (FIG. 7).

Figure 8:
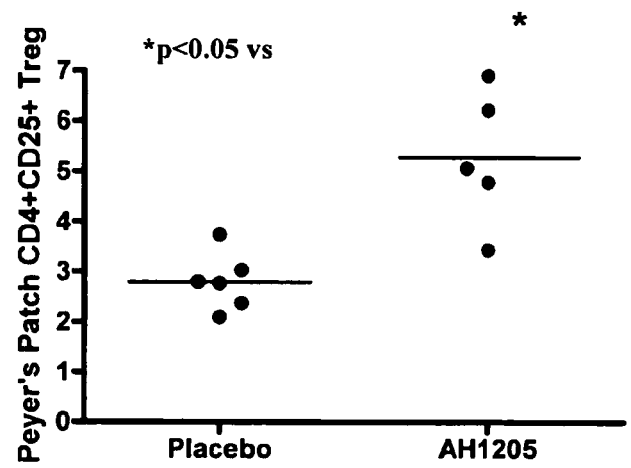
FIG. 8 is a graph showing the percentage of Payer's patch cells in the CD4+population that are also CD25+, as assessed by flow cytometry.

The % of cells in the CD4+ population that were also CD25+ was determined (FIG. 8). The *Bifidobacterium longum* AH1205 fed group had significantly more CD4+ T cells that were CD25+ (i.e. T-Regulatory cells) than their placebo-fed counterparts. This suggests that the % of T-Regulatory cells within the CD4+ population was increased significantly by feeding with AH1205.

The number of CD4+CD25+ FoxP3+ cells in the whole splenocyte populations of probiotic or placebo-fed mice was also determined. The number of CD4+CD25+ T-Regulatory cells expressing FoxP3 was unchanged in the spleens of probiotic fed mice relative to placebo or unfed mice.

EXAMPLE 5

Germ Free Model

Germ free mice were purchased at 6 weeks of age and maintained in the germ-free unit at the biological services unit in UCC. Animals consumed the probiotic strain *Bifidobacterium longum* AH1205 for 9 days or remained germ free. Induction of T regulatory cells was assessed by flow cytometry and cytokine levels were quantified by CBA.

AH1205 transit was assessed by measuring *bifidobacterial* counts on selective agar over the course of the study. AH1205 did not transit the gut of germ free mice in measurable numbers even though approximately $1 \times 10^9$ organisms were administered daily. The results suggests that additional microbial or host factors are required for *bifidobacterial* survival within the gut.

Figure 9:
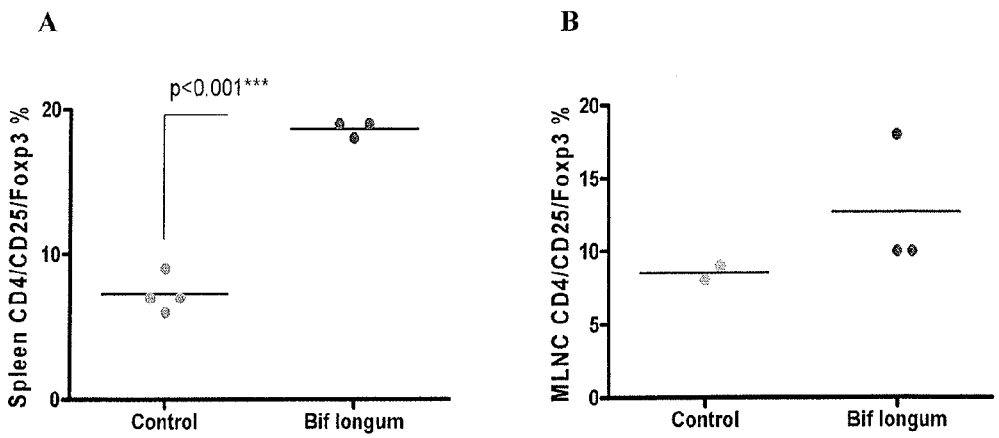
FIGS. 9 A and B are graphs showing the percentage of CD4/CD25+cells expressing the transcription factor Foxp3 is significantly upregulated in germ free mice consuming AH1205. (A)=spleen cells, (B)=MLNC cells (n=4/group for spleen assay, n=2/3 for MLNC assay).

While AH1205 did not transit the gut in detectable numbers, the bacteria did interact with the host immune system. The numbers of CD4+CD25+ Foxp3+ cells in the mesenteric lymph node and spleen of AH1205 fed germ-free animals was significantly increased following 9 days of feeding (FIG. 9). Total CD3/CD4 or CD3/CD8 counts remained unaltered.

Figure 10:
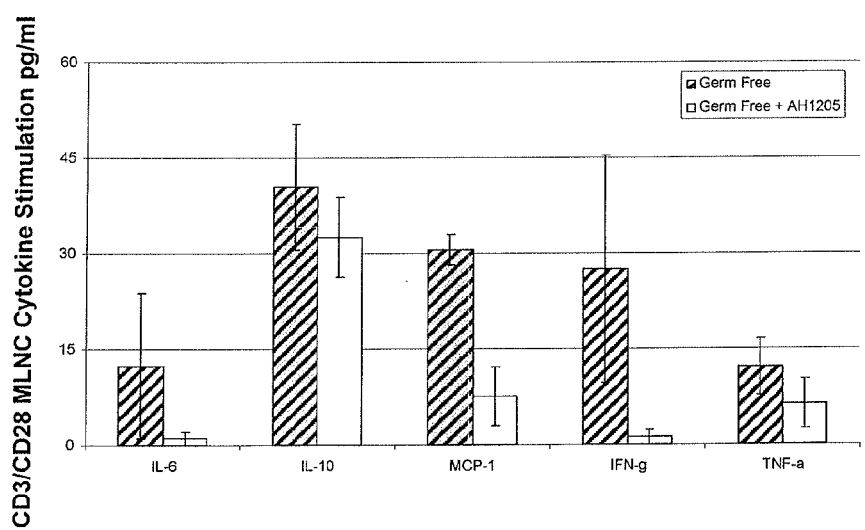
FIG. 10 is a graph showing that the level of cytokines IL-6, MCP-1 and IFN-γ secreted by CD3/CD28 stimulated MLNC cultures was reduced when germ—free mice consumed *Bifidobacterium longum* AH1205. Results are expressed as the mean per group+/–standard error. (n=4/group).
Figure 11:
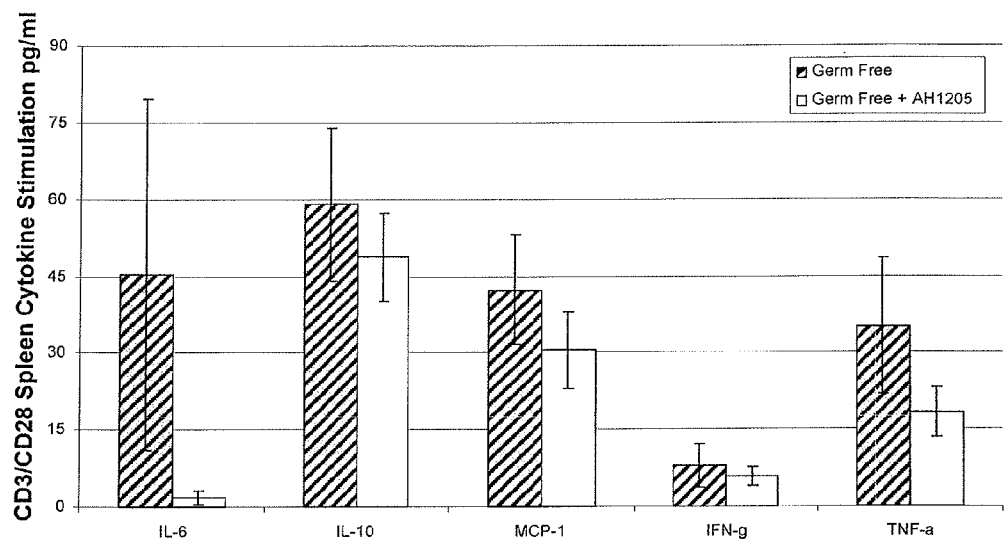
FIG. 11 is a graph showing that the level of cytokines IL-6 and TNF-α secreted by CD3/CD28 stimulated splenocyte cultures was reduced when germ—free mice consumed *Bifidobacterium longum* AH1205. Results are expressed as the mean per group+/–standard error (n=4/group).

Isolated mesenteric lymph node cells (MLNC) and splenocytes were stimulated in vitro with anti-CD3/CD28 antibodies or LPS or remained un-stimulated as negative controls. MLNC secretion of IL-6 and IFN-γ, following CD3/CD28 stimulation, was substantially decreased in culture supernatants while MCP-1 levels were significantly suppressed when mice were pre-fed AH1205 (FIG. 10). IL-10 levels remained similar between the groups. Splenocyte release of IL-6 and TNF-α was substantially, but not significantly, decreased when pre-fed AH1205 (FIG. 11). No significant differences were noted for the un-stimulated or LPS stimulated cultures but overall we observed less pro-inflammatory cytokine production from the Bifidobacteria AH1205-fed animals.

EXAMPLE 6

Stability Results

Figure 12:
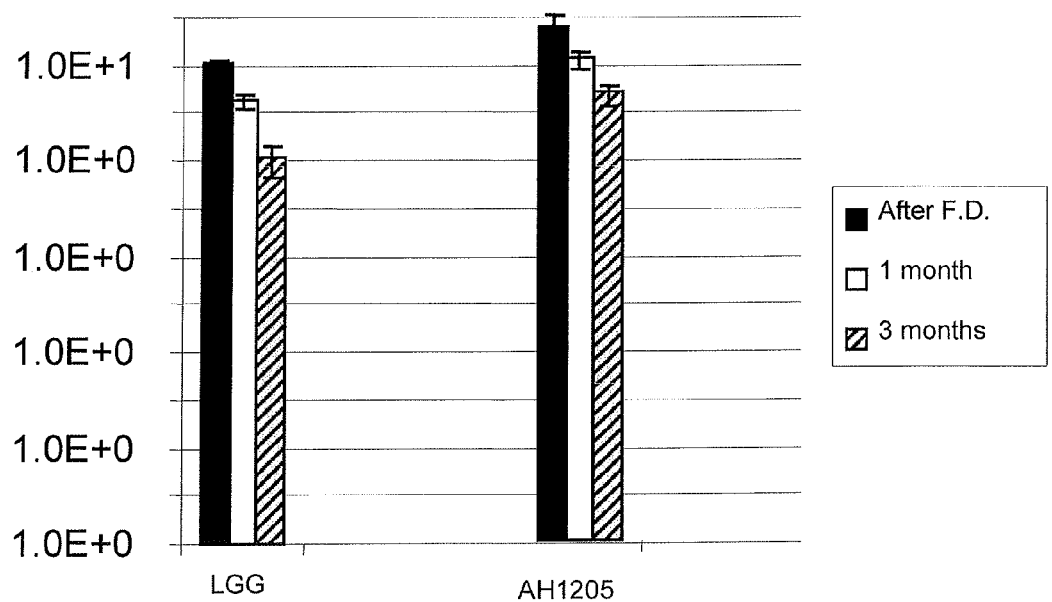
FIG. 12 is a graph illustrating the stability of probiotic strain AH1205 over 3 months compared to *Lactobacillus* GG.

The stability of the probiotic strain AH1205, varied over 3 months at 30° C. (FIG. 12)

*Lactobacillus* GG was a poor performer over the test period with a 2 log drop over the 3 month period whereas strain AH 1205 declined in viability by up to approximately 1 log over the same test period.

Immunomodulation

The human immune system plays a significant role in the aetiology and pathology of a vast range of human diseases. Hyper and hypo-immune responsiveness results in, or is a component of, the majority of disease states. One family of biological entities, termed cytokines, are particularly important to the control of immune processes. Pertubances of these delicate cytokine networks are being increasingly associated with many diseases. These diseases include but are not limited to inflammatory disorders, immunodeficiency, inflammatory bowel disease, irritable bowel syndrome, cancer (particularly those of the gastrointestinal and immune systems), diarrhoeal disease, antibiotic associated diarrhoea, paediatric diarrhoea, appendicitis, autoimmune disorders, multiple sclerosis, Alzheimer's disease, rheumatoid arthritis, coeliac disease, diabetes mellitus, organ transplantation, bacterial infections, viral infections, fungal infections, periodontal disease, urogenital disease, sexually transmitted disease, HIV infection, HIV replication, HIV associated diarrhoea, surgical associated trauma, surgical-induced metastatic disease, sepsis, weight loss, anorexia, fever control, cachexia, wound healing, ulcers, gut barrier function, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, epidermal disorders, psoriasis and acne vulgaris. The effects on cytokine production are specific for each of the probiotic strains examined. Thus specific probiotic strains may be selected for normalizing an exclusive cytokine imbalance particular for a specific disease type. Customization of disease specific therapies can be accomplished using either a single strain of AH1205 or mutants or variants thereof or a selection of these strains.

Immune Education

The enteric flora is important to the development and proper function of the intestinal immune system. In the absence of an enteric flora, the intestinal immune system is underdeveloped, as demonstrated in germ free animal models, and certain functional parameters are diminished, such as macrophage phagocytic ability and immunoglobulin production (10). The importance of the gut flora in stimulating non-damaging immune responses is becoming more evident. The increase in incidence and severity of allergies in the western world has been linked with an increase in hygiene and sanitation, concomitant with a decrease in the number and range of infectious challenges encountered by the host. This lack of immune stimulation may allow the host to react to non-pathogenic, but antigenic, agents resulting in allergy or autoimmunity. Deliberate consumption of a series of non-pathogenic immunomodulatory bacteria would provide the host with the necessary and appropriate educational stimuli for proper development and control of immune function.

Inflammation

Inflammation is the term used to describe the local accumulation of fluid, plasma proteins and white blood cells at a site that has sustained physical damage, infection or where there is an ongoing immune response. Control of the inflammatory response is exerted on a number of levels (11). The controlling factors include cytokines, hormones (e.g. hydrocortisone), prostaglandins, reactive intermediates and leukotrienes. Cytokines are low molecular weight biologically active proteins that are involved in the generation and control of immunological and inflammatory responses, while also regulating development, tissue repair and haematopoiesis. They provide a means of communication between leukocytes themselves and also with other cell types. Most cytokines are pleiotrophic and express multiple biologically overlapping activities. Cytokine cascades and networks control the inflammatory response rather than the action of a particular cytokine on a particular cell type (12). Waning of the inflammatory response results in lower concentrations of the appropriate activating signals and other inflammatory mediators leading to the cessation of the inflammatory response. TNFα is a pivotal proinflammatory cytokine as it initiates a cascade of cytokines and biological effects resulting in the inflammatory state. Therefore, agents which inhibit TNFα are currently being used for the treatment of inflammatory diseases, e.g. INFLIXIMAB.

Pro-inflammatory cytokines are thought to play a major role in the pathogenesis of many inflammatory diseases, including inflammatory bowel disease (IBD). Current therapies for treating IBD are aimed at reducing the levels of these pro-inflammatory cytokines, including IL-8 and TNFα. Such therapies may also play a significant role in the treatment of systemic inflammatory diseases such as rheumatoid arthritis.

The strains of the present invention may have potential application in the treatment of a range of inflammatory diseases, particularly if used in combination with other anti-inflammatory therapies, such as non-steroid anti-inflammatory drugs (NSAIDs) or INFLIXIMAB.

Cytokines and Cancer

The production of multifunctional cytokines across a wide spectrum of tumour types suggests that significant inflammatory responses are ongoing in patients with cancer. It is currently unclear what protective effect this response has against the growth and development of tumour cells in vivo. However, these inflammatory responses could adversely affect the tumour-bearing host. Complex cytokine interactions are involved in the regulation of cytokine production and cell proliferation within tumour and normal tissues (13,14). It has long been recognized that weight loss (cachexia) is the single most common cause of death in patients with cancer and initial malnutrition indicates a poor prognosis. For a tumour to grow and spread it must induce the formation of new blood vessels and degrade the extracellular matrix. The inflammatory response may have significant roles to play in the above mechanisms, thus contributing to the decline of the host and progression of the tumour. Due to the anti-inflammatory properties of *Bifidobacterium longum infantis* these bacterial strains they may reduce the rate of malignant cell transformation. Furthermore, intestinal bacteria can produce, from dietary compounds, substances with genotoxic, carcinogenic and tumour-promoting activity and gut bacteria can activate pro-carcinogens to DNA reactive agents (15). In general, species of *Bifidobacterium* have low activities of xenobiotic metabolizing enzymes compared to other populations within the gut such as *bacteroides*, eubacteria and clostridia. Therefore, increasing the number of *Bifidobacterium* bacteria in the gut could beneficially modify the levels of these enzymes.

Vaccine/Drug Delivery

The majority of pathogenic organisms gain entry via mucosal surfaces. Efficient vaccination of these sites protects against invasion by a particular infectious agent. Oral vaccination strategies have concentrated, to date, on the use of attenuated live pathogenic organisms or purified encapsulated antigens (16). Probiotic bacteria, engineered to produce antigens from an infectious agent, in vivo, may provide an attractive alternative as these bacteria are considered to be safe for human consumption (GRAS status).

Murine studies have demonstrated that consumption of probiotic bacteria expressing foreign antigens can elicit protective immune responses. The gene encoding tetanus toxin fragment C (TTFC) was expressed in *Lactococcus* lactis and mice were immunized via the oral route. This system was able to induce antibody titers significantly high enough to protect the mice from lethal toxin challenge. In addition to antigen presentation, live bacterial vectors can produce bioactive compounds, such as immunostimulatory cytokines, in vivo. *L. lactis* secreting bioactive human IL-2 or IL-6 and TTFC induced 10-15 fold higher serum IgG titres in mice immunized intranasally (17). However, with this particular bacterial strain, the total IgA level was not increased by coexpression with these cytokines. Other bacterial strains, such as *Streptococcus gordonii*, are also being examined for their usefulness as mucosal vaccines. Recombinant *S. gordonii* colonizing the murine oral and vaginal cavities induced both mucosal and systemic antibody responses to antigens expressed by this bacterial (18). Thus oral immunization using probiotic bacteria as vectors would not only protect the host from infection, but may replace the immunological stimuli that the pathogen would normally elicit thus contributing to the immunological education of the host.

Prebiotics

The introduction of probiotic organisms is accomplished by the ingestion of the micro-organism in a suitable carrier. It would be advantageous to provide a medium that would promote the growth of these probiotic strains in the large bowel. The addition of one or more oligosaccharides, polysaccharides, or other prebiotics enhances the growth of lactic acid bacteria in the gastrointestinal tract. Prebiotics refers to any non-viable food component that is specifically fermented in the colon by indigenous bacteria thought to be of positive value, e.g. bifidobacteria, lactobacilli. Types of prebiotics may include those that contain fructose, xylose, soya, galactose, glucose and mannose. The combined administration of a probiotic strain with one or more prebiotic compounds may enhance the growth of the administered probiotic in vivo resulting in a more pronounced health benefit, and is termed synbiotic.

Other Active Ingredients

It will be appreciated that the probiotic strains may be administered prophylactically or as a method of treatment either on its own or with other probiotic and/or prebiotic materials as described above. In addition, the bacteria may be used as part of a prophylactic or treatment regime using other active materials such as those used for treating inflammation or other disorders especially those with an immunological involvement. Such combinations may be administered in a single formulation or as separate formulations administered at the same or different times and using the same or different routes of administration.

The invention is not limited to the embodiments herein before described which may be varied in detail.

REFERENCES

1. McCracken V. J. and Gaskins H. R. Probiotics and the immune system. In: *Probiotics a critical review*, Tannock, G W (ed), Horizon Scientific Press, UK. 1999, p. 85-113.
2. Savage D. C. Interaction between the host and its microbes. In: *Microbial Ecology of the Gut*, Clark and Bauchop (eds), Academic Press, London. 1977, p. 277-310.
3. Kagnoff M. F. Immunology of the intestinal tract. *Gastroenterol.* 1993; 105 (5): 1275-80.
4. Lamm M. E. Interaction of antigens and antibodies at mucosal surfaces. *Ann. Rev. Microbiol.* 1997; 51: 311-40.
5. Raychaudhuri S., Rock K L. Fully mobilizing host defense: building better vaccines. *Nat biotechnol.*, 1998; 16: 1025-31.
6. Stallmach A., Strober W, MacDonald T T, Lochs H, Zeitz M. Induction and modulation of gastrointestinal inflammation. *Immunol. Today,* 1998; 19 (10): 438-41.
7. de Waal Malefyt R, Haanen J, Spits H, Roncarolo M G, to Velde A, Figdor C, Johnson K, Kastelein R, Yssel H, de Vries J E. Interleukin 10 (IL-10) and viral IL-10 strongly reduce antigen-specific human T cell proliferation by diminishing the antigen-presenting capacity of monocytes via downregulation of class II major histocompatibility complex expression. J Exp Med 1991 Oct. 1; 174(4):915-24.
8. Masco L, Huys G, Gevers D, Verbrugghen L, Swings J. Identification of *Bifidobacterium* species using rep-PCR fingerprinting. Syst Appl Microbiol. 2003 November; 26(4):557-63. PMID: 14666984.
9. Tagg, J R, Dajani, A S, Wannamaker, L W. Bacteriocins of Gram positive bacteria. *Bacteriol Rev.* 1976; 40: 722-756.
10. Crabbe P. A., H. Bazin, H. Eyssen, and J. F. Heremans. The normal microbial flora as a major stimulus for proliferation of plasma cells synthesizing IgA in the gut. The germ free intestinal tract. *Into. Arch. Allergy Appl Immunol,* 1968; 34: 362-75.
11. Henderson B., Poole, S and Wilson M. 1998. In "Bacteria-Cytokine interactions in health and disease. Portland Press, 79-130.
12. Arai K I, Lee F, Miyajima A, Miyatake S, Arai N, Yokota T. Cytokines: coordinators of immune and inflammatory responses. *Annu Rev Biochem* 1990; 59:783-836.
13. McGee D W, Bamberg T, Vitkus S J, McGhee J R. A synergistic relationship between TNF-alpha, IL-1 beta, and TGF-beta 1 on IL-6 secretion by the IEC-6 intestinal epithelial cell line. *Immunology* 1995 September; 86(1):6-11.
14. Wu S, Meeker W A, Wiener J R, Berchuck A, Bast R C Jr, Boyer C M. Transfection of ovarian cancer cells with tumour necrosis factor alpha (TNF-alpha) antisense mRNA abolishes the proliferative response to interleukin-1 (IL-1) but not TNF-alpha. *Gynecol Oncol* 1994 April; 53(1):59-63.
15. Rowland I. R. Toxicology of the colon: role of the intestinal microflora. In: Gibson G. R. (ed). *Human colonic bacteria: role in nutrition, physiology and pathology,* 1995, pp 155-174. Boca Raton CRC Press.
16. Walker, R. I. New strategies for using mucosal vaccination to achieve more effective immunization. *Vaccine,* 1994; 12: 387-400.
17. Steidler L., K. Robinson, L. Chamberlain, K. M Scholfield, E. Remaut, R. W. F. Le Page and J. M. Wells. Mucosal delivery of murine interleukin-2 (IL-2) and IL-6 by recombinant strains of *Lactococcus* lactis coexpressing antigen and cytokine. *Infect. Immun.*, 1998; 66:3183-9.
18. Medaglini D., G. Pozzi, T. P. King and V. A. Fischetti. Mucosal and systemic immune responses to a recombinant protein expressed on the surface of the oral commensal bacterium *Streptococcus gordonii* after oral colonization. *Proc. Natl. Acad. Sci. USA*, 1995; 92:6868-72 McCracken V. J. and Gaskins H. R, 'Probiotics a critical review', Horizon Scientific Press, UK 1999, p. 278.
19. Marson, A., Kretschmer, K., Frampton, G. M., Jacobsen, E. S., Polansky, J. K., MacIsaac, K. D., Levine, S. S., Fraenkel, E., von Boehmer, H and Young, R. A. Foxp3 occupancy and regulation of key target genes during T-cell stimulation. *Letters to Nature*, 2007

---

The invention claimed is:

1. An isolated strain of *Bifidobacterium* deposited at NCIMB with accession number 41387.

2. The *Bifidobacterium* strain as claimed in claim 1 in the form of viable cells.

3. The *Bifidobacterium* strain as claimed in claim 1 in the form of non-viable cells.

4. A formulation comprising an isolated strain of *Bifidobacterium* deposited at NCIMB with accession number 41387.

5. The formulation as claimed in claim 4 which further comprises a probiotic material.

6. The formulation as claimed in claim 4 which further comprises a prebiotic material.

7. The formulation as claimed in claim 4 further comprising an ingestable carrier.

8. The formulation as claimed in claim 7 wherein the ingestable carrier is a pharmaceutically acceptable carrier.

9. The formulation as claimed in claim 7 wherein the ingestable carrier is a food product.

10. The formulation as claimed in claim 1 which further comprises a protein and/or peptide, a lipid, a carbohydrate, a vitamin, mineral and/or trace element.

11. The formulation as claimed in claim 4 wherein the *Bifidobacterium* strain is present in an amount of more than $10^6$ cfu per gram of the formulation.

12. The formulation as claimed in claim 4 which further comprises an adjuvant.

13. The formulation as claimed in claim 4 which further comprises a bacterial component.

14. The formulation as claimed in claim 4 which further comprises a drug entity.

15. The formulation as claimed in claim 4 which further comprises a biological compound.

16. A food stuff comprising an isolated strain of *Bifidobacterium* deposited at NCIMB with accession number 41387.

17. A medicament comprising an isolated strain of *Bifidobacterium* deposited at NCIMB with accession number 41387.

18. An anti-inflammatory biotherapeutic agent comprising an isolated strain of *Bifidobacterium* s deposited at NCIMB with accession number 41387.

19. An anti-inflammatory biotherapeutic agent for reducing the levels of pro-inflammatory cytokines comprising a *Bifidobacterium* strain as claimed in claim 1.

20. The formulation as claimed in claim 8 wherein the pharmaceutically acceptable carrier is in the form of a capsule, tablet or powder.

21. The formulation as claimed in claim 9 wherein the food product is selected from the group consisting of: acidified milk, yogurt, frozen yogurt, milk powder, milk concentrate, cheese spreads, dressings and beverages.

22. The formulation as claimed in claim 10 wherein the protein and/or peptides are rich in glutamine/glutamate.

* * * * *

UNITED STATES PATENT AND TRADEMARK OFFICE
CERTIFICATE OF CORRECTION

PATENT NO.       : 8,709,398 B2                                              Page 1 of 1
APPLICATION NO. : 12/450451
DATED            : April 29, 2014
INVENTOR(S)      : MacSharry et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1162 days.

Signed and Sealed this

Twenty-ninth Day of September, 2015

Michelle K. Lee
*Director of the United States Patent and Trademark Office*